(12) United States Patent
Bille

(10) Patent No.: US 7,798,641 B2
(45) Date of Patent: Sep. 21, 2010

(54) FINITE ELEMENT MODEL OF A KERATOCONIC CORNEA

(75) Inventor: Josef F. Bille, Heidelberg (DE)

(73) Assignee: Heidelberg Engineering GmbH, Heidelberg (DE)

( * ) Notice: Subject to any disclaimer, the term of this patent is extended or adjusted under 35 U.S.C. 154(b) by 32 days.

(21) Appl. No.: 12/205,420

(22) Filed: Sep. 5, 2008

(65) Prior Publication Data

US 2010/0060854 A1    Mar. 11, 2010

(51) Int. Cl.
A61B 3/14    (2006.01)
(52) U.S. Cl. .................. 351/206; 351/246; 351/212
(58) Field of Classification Search ................ 351/206
See application file for complete search history.

(56) References Cited

U.S. PATENT DOCUMENTS

| 3,769,963 | A |   | 11/1973 | Goldman et al. |         |
|-----------|---|---|---------|----------------|---------|
| 4,770,172 | A |   | 9/1988  | L'Esperance, Jr. |       |
| 4,903,695 | A |   | 2/1990  | Warner et al.  |         |
| 5,521,657 | A | * | 5/1996  | Klopotek       | 351/212 |
| 5,870,167 | A | * | 2/1999  | Knopp et al.   | 351/212 |
| 5,993,438 | A |   | 11/1999 | Juhasz et al.  |         |
| 2002/0077797 | A1 |   | 6/2002 | Hall         |         |
| 2004/0021826 | A1 | * | 2/2004 | Sarver et al. | 351/212 |
| 2006/0274269 | A1 | * | 12/2006 | Koest        | 351/246 |
| 2007/0291228 | A1 | * | 12/2007 | Huang et al. | 351/212 |
| 2008/0086048 | A1 | * | 4/2008 | Dupps et al.  | 600/405 |
| 2009/0190093 | A1 | * | 7/2009 | Tanassi et al. | 351/208 |
| 2009/0303441 | A1 | * | 12/2009 | Lieberman et al. | 351/246 |

FOREIGN PATENT DOCUMENTS

WO    2007139927    12/2007
WO    2008042314    4/2008

OTHER PUBLICATIONS

Zhang, Hongwei, "Finite Element Modeling of the Cornea and its Application in the Refractive Surgery", A Study of Aberrations in the Human Eye by Zernike Phase Plate Precompensation and Finite Element Modeling Methods, Chapter 1, pp. 1-26, 2007, Heilongjiang, China.

Jouve, Francois and Hanna, Khalil, "Computer Simulations of Refractive Surgery and Accomodation Mechanisms", IUTAM Symposium on Synthesis in Bio Solid Mechanics. Springer Netherlands, (2006).

Ruiz, L. A., MD. "Preliminary clinical results of non-invasive, intrastromal correction of presbyopia using the FEMTEC femtosecond laser system", Hawaiian Eye Meeting (2008).

(Continued)

*Primary Examiner*—Jessica T Stultz
(74) *Attorney, Agent, or Firm*—Nydegger & Associates

(57) ABSTRACT

A system and method for diagnosing the onset of keratoconus in a cornea requires subjecting the cornea of an eye to a pressure that changes its shape. A topography of the cornea's anterior surface (possibly, the posterior surface also) is mapped. The mapped topography is then fitted on a mathematical model of the cornea. Measurements corresponding to biomechanical parameters in the cornea are then taken from the model. Next, a computer is used to evaluate the biomechanical parameters to diagnose whether the cornea is keratoconic.

17 Claims, 3 Drawing Sheets

OTHER PUBLICATIONS

Crouch, Jessica R., Merriam, John C., and Crouch, Earl R. "Finite Element Model of Cornea Deformation." Medical Image Computing and Computer-Assisted Intervention. Springer Berlin. Heidelberg, Germany, 2005. 591-598.

Anderson, K., El-Sheikh, A., & Newson, T., "Application of structural analysis to the mechanical behaviour of the cornea", The Royal Society, (2004).

Waldman, Lewis et al., "Computational Mechanics of the Sclera and Optic Nerve Head (ONH): Effects of ONH Size and Pressure Range",BioMed2008-38051, Proceedings of ASME BioMed08, Irvine, CA, (2008).

Anderson, K., El-Sheikh, A., & Newson, T., "FEA of the biomechanics of procine corneas", The Structural Engineer, (2004).

Scherer, K.,P., Eggert, H., Guth, H., and Stiller, P., "Biomechanical simulations for refractive corneal eye surgery", Proceedings of the IASTED International Conference, (2001).

* cited by examiner

FINITE ELEMENT MODEL OF A KERATOCONIC CORNEA

FIELD OF THE INVENTION

The present invention pertains generally to ophthalmic diagnostic equipment and procedures. More particularly, the present invention pertains to diagnostic systems and methods that employ mathematical models of the cornea for diagnosing corneal diseases, such as keratoconus. The present invention is particularly, but not exclusively, useful as a system and method for making an early diagnosis of keratoconus, to determine whether a cornea is a proper candidate for subsequent refractive surgical procedures.

BACKGROUND OF THE INVENTION

By definition, keratoconus is a non-inflammatory, usually bilateral protrusion of the cornea, the apex being displaced downward and nasally. Essentially, keratoconus is caused by a thinning of the cornea that will typically result in asymmetric astigmatism. Another aspect of the disease, however, also deserves consideration. Specifically, this consideration is the fact that keratoconus causes a loss of corneal tissue that may effectively preclude an individual from pursuing particular refractive surgical procedures for vision correction. For example, due to the inherent loss of corneal tissue, keratoconus would be contraindicative for procedures that involve the removal of corneal tissue (e.g. the well-known LASIK surgery).

In the early stages of the disease, keratoconus is not easily detected. Specifically, the pronounced change in the shape of the cornea that is characteristic of advanced keratoconus, is not noticeably evident in the early stages. Nevertheless, there are structural weaknesses in the corneal tissue, caused by lamella crossover in the early stages of the disease, that portend the disease. It is extremely difficult, however, if not impossible to locate and directly measure the biomechanical stresses and strains that are characteristic of these weaknesses.

Anatomically, the cornea of an eye comprises five identifiable layers of tissue. In an anterior-posterior direction these layers are: epithelium, Bowman's membrane, stroma, Descemet's membrane, and endothelium. The stroma forms about 90% of the corneal thickness, with Bowman's membrane forming most of the remaining thickness. Though smaller than the stroma, Bowman's membrane is around five times stronger and is more elastic than is stromal tissue. The remaining layers (i.e. epithelium, Descemet's membrane, and endothelium) provide negligible structural strength for the cornea. Accordingly, based on layer thickness and relative structural considerations (i.e. biomechanical parameters) for Bowman's membrane and the stroma, a mathematical model of a cornea can be established using well known mathematical techniques.

Unlike the difficulties mentioned above that are encountered in measuring biomechanical characteristics of corneal tissue, surfaces of the cornea can be more easily defined. In particular, respective topographies for the anterior and posterior surfaces of a cornea can be obtained using known imaging techniques (e.g. second harmonic generation imaging). Further, it is known that the shape of a cornea, as determined by its surface topographies, is a consequence of the stress-strain relationships experienced by tissues inside the cornea.

In light of the above, it is an object of the present invention to provide a system and method for diagnosing a keratoconic cornea at the onset of the disease, prior to any observably noticeable change in the anatomical shape of the cornea. Another object of the present invention is to provide a system and method for determining whether a cornea is a proper candidate for subsequent refractive surgical procedures. Yet another object of the present invention is to provide a system and method for diagnosing a keratoconic cornea that is simple to employ, is easy to use and is comparatively cost effective.

SUMMARY OF THE INVENTION

In accordance with the present invention, a system and method for diagnosing the onset of keratoconus in a cornea requires mapping the anterior surface of the cornea of an eye. Once the eye has been mapped, the resultant topography is fitted onto a finite element model (FEM), and the consequent tissue parameters are evaluated. Preferably, the mapping is accomplished while the eye is subjected to an externally imposed pressure that will be less than about 14 kPa. Mapping, however, can also be made with no added pressure, or at a series of different pressures. In any event, if employed, pressure is used to change the shape of the cornea and thereby enhance the resultant topography measurements. The mapped topographies are then fitted on a mathematical model of the cornea and biomechanical parameters in the cornea are taken from the model for the respective corneal configurations. Next, a computer is used to evaluate the biomechanical parameters. Based on this evaluation, a diagnosis is made as to whether the cornea is keratoconic. In this context, a topography mapped while the eye is under pressure may be more likely to give accurate information and, though mapping only one topography may suffice, additional information from different pressure topographies will improve precision.

In greater detail, to perform a diagnostic procedure in accordance with the present invention, a topography "$T_a$" of the anterior surface of the cornea is mapped and recorded. As mentioned above, this is preferably done while the eye is under pressure. If desired, a respective topography of the posterior surface of the cornea, "$T_p$" can also be similarly mapped and recorded. Once the topographies "$T_a$", and "$T_p$" (if used), have been mapped and recorded, they are appropriately fitted onto a mathematical model of a cornea. For purposes of the present invention, the model preferably comprises a plurality of finite elements, wherein each element corresponds to a particular location in the actual cornea, and each element is defined by a plurality of parameters. Thus, for example, fitting "$T_a$", and possibly "$T_p$", onto the model obtains a set of parameters for the model. Importantly, these parameters are representative of the cornea in a configuration, when the eye is under conditions established by a predetermined intraocular pressure. Preferably, this pressure is less than 14 kPa. Further, each parameter is indicative of a biomechanical property (characteristic) of tissue at a particular location in the cornea. Collectively they can be used to evaluate the eye.

As indicated above, additional sets of parameters can be obtained at different pressure levels in the eye. Also, each parameter in each of these sets is indicative of a biomechanical property (characteristic) of tissue at a particular location in the cornea, at the particular pressure. Typically, these conditions are established with representative intraocular pressures that are less than approximately 14 kPa. Importantly, each parameter in a set of parameters corresponds to a respective parameter at a same location in another set of parameters. Thus, using a computer, the different sets of parameters are compared with each other to evaluate changes in biomechanical properties of the cornea. In turn, these changes are used for diagnosing whether the cornea is keratoconic.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
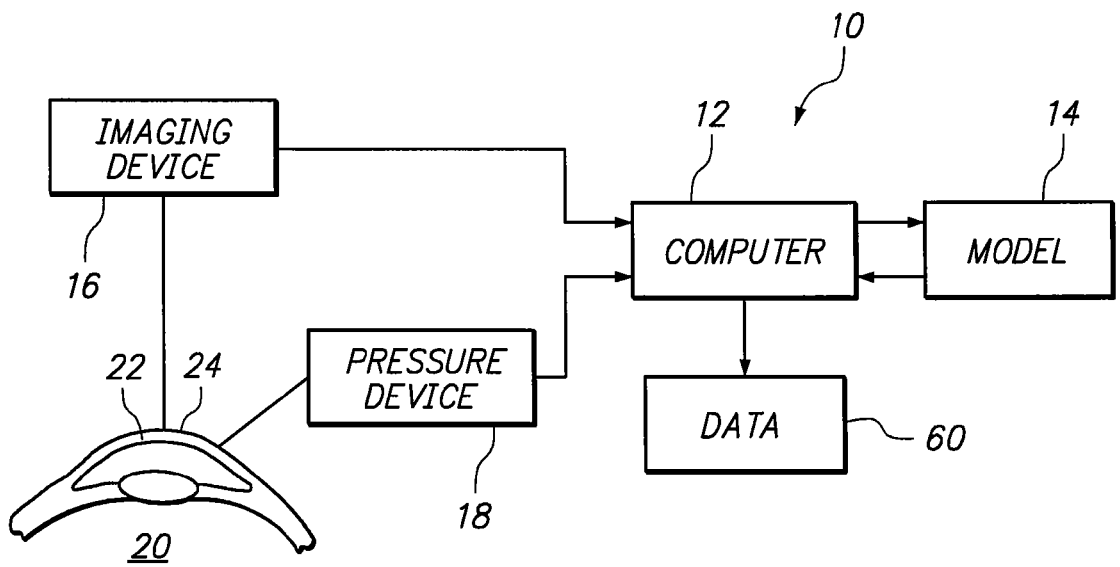
FIG. 1 is a schematic representation of the system of the present invention.

Referring initially to FIG. 1, a system for diagnosing keratoconus in accordance with the present invention is shown and is generally designated 10. As shown, the system 10 includes a computer 12 that is electronically interconnected with a mathematical model 14. Also interconnected with the computer 12 are an imaging device 16 and a pressure device 18. As indicated in FIG. 1, the imaging device 16 and the pressure device 18 are positioned to interact with an eye 20 of a patient (not shown). More particularly, the devices 16 and 18 are positioned to interact with the cornea 22 of the eye 20.

Figure 2:
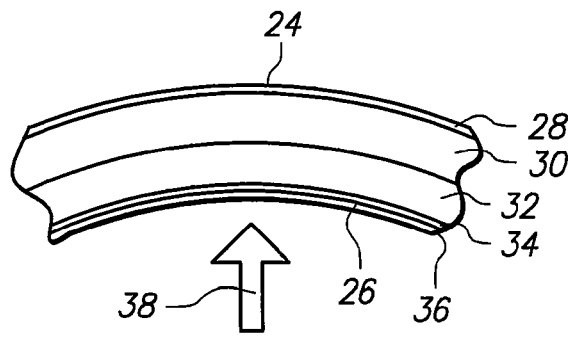
FIG. 2 is a cross section view of a cornea of an eye.

In FIG. 2, a cross section of the cornea 22 shows that, anatomically, the cornea 22 has five different identifiable layers of tissue. Between the anterior surface 24 and the posterior surface 26 of the cornea 22, and going in an anterior-posterior direction, the layers of the cornea 22 are: epithelium 28; Bowman's membrane 30; stroma 32; Descemet's membrane 34; and endothelium 36. Structurally, Bowman's membrane 30 and the stroma 32 of cornea 22 are much more significant than the other three layers. So much so that, for strength considerations, the epithelium 28, Descemet's membrane 34 and the endothelium 36 can be considered mathematically negligible.

For purposes of the present invention, the model 14 is a mathematical model of the cornea 22. Preferably, the model 14 is a finite element model that includes a plurality of different elements, wherein each element in the model 14 is defined by a plurality of mathematical parameters. And, importantly, each parameter in every element of the model 14 is representative of tissue qualities (i.e. biomechanical characteristics) in the cornea 22. Further, it is important that each element of the model 14 corresponds to a particular anatomical location in the cornea 22. In a preferred embodiment of the model 14, elements are included that will represent both Bowman's membrane 30 and the stroma 32. The actual set-up for the model 14 can be accomplished using well-known mathematical techniques.

As mentioned above, the system 10 is to be primarily used for diagnosing keratoconus of the eye 20 prior to the onset of the disease. As also mentioned above, even before the disease is observably noticeable, weaknesses in the cornea 22 are present. Accordingly, these weaknesses can be expected to be manifested under certain conditions. Specifically, the present invention envisions that a proper disclosure of these weaknesses can be obtained by imposing a differential in the intraocular pressure against the posterior surface 26 of the cornea 22. Such a pressure differential is indicated by the arrow 38 in FIG. 2. The result is an observable change in the shape (i.e. topography) of the cornea 22. It is the nature and the extent of this change, however, that is of value for diagnosing keratoconus.

Figure 3:
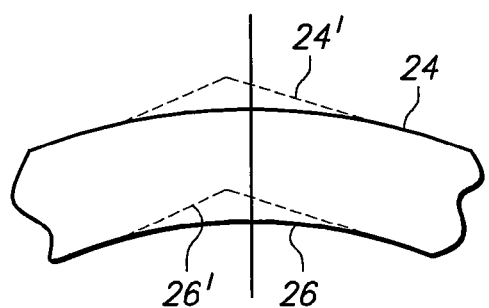
FIG. 3 is a cross section view of a cornea of an eye under a first pressure condition, with a view of the cornea under a second pressure condition superposed thereon.

An example of the consequence of a pressure differential 38 on the cornea 22 of a keratoconic eye 20 can be seen with reference to FIG. 3. There it is to be appreciated that prior to imposing the pressure differential 38, the cornea 22 is subjected to a normal intraocular pressure (e.g. 2 kPa). Under this normal pressure, the anterior surface 24 and the posterior surface 26 of the cornea 22 will be substantially as shown by the solid lines in FIG. 3. If the eye 20 is keratoconic, a topography indicative of this condition may not be discernable. Under the influence of the pressure differential 38, however, (e.g. 10 kPa), the anterior surface 24' and the posterior surface 26' are forced into another configuration where a keratoconic condition is more pronounced. On this point, empirical data indicates that tissue parameters of a normal eye are as much as five times greater than corresponding parameters for a keratoconic eye. A consequence of this difference for a keratoconic eye 20 is shown in FIG. 3 where a pressured configuration (i.e. dashed lines) is shown superposed on an unpressurized configuration (i.e. solid lines). In contrast with this, a normal eye will not exhibit a discernable configuration change in its topography at different pressure levels.

Figure 4:
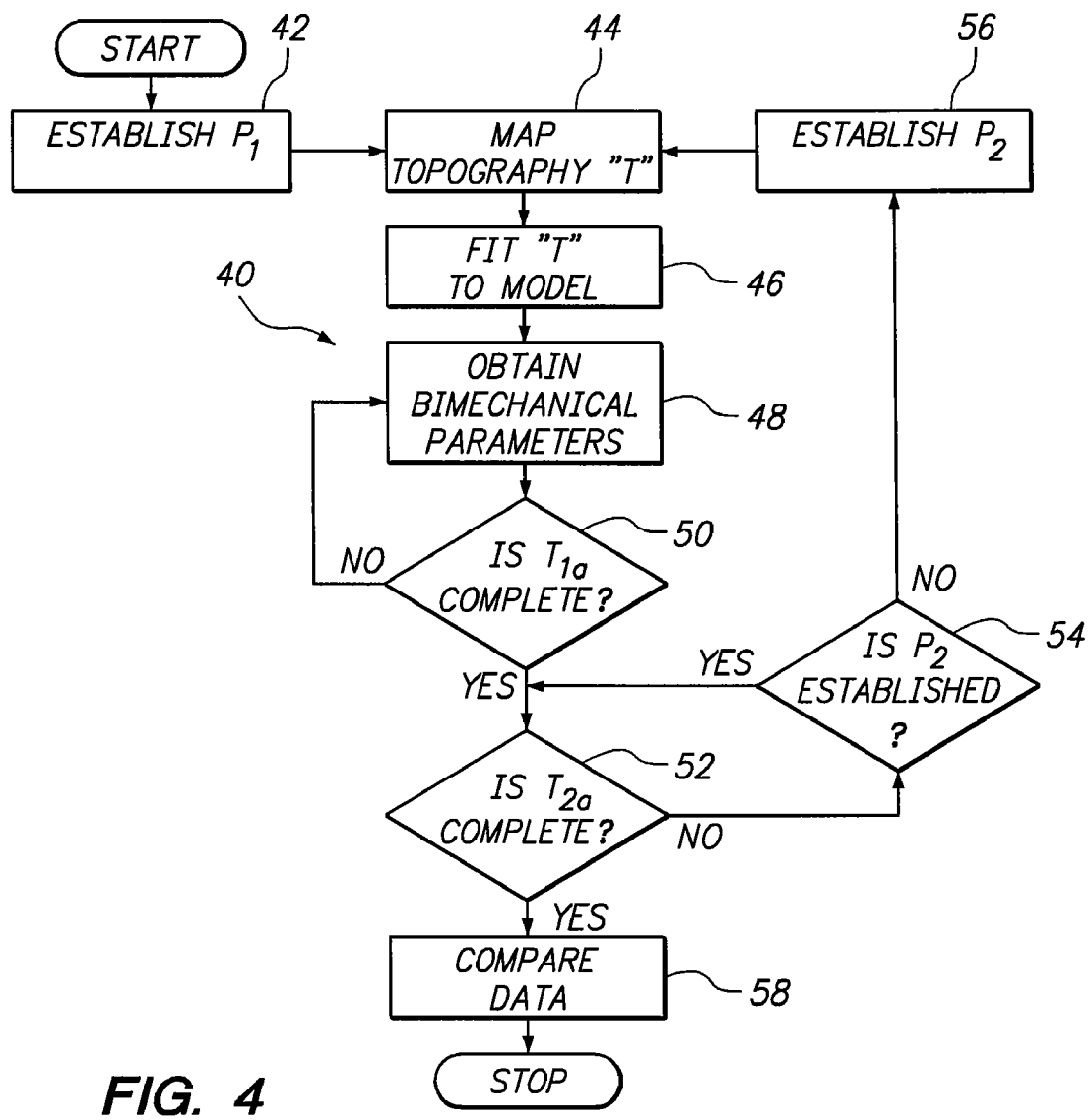
FIG. 4 is a logic chart for the operation of the system of the present invention.

The logic chart that is generally designated 40 in FIG. 4, is exemplary of an operation of the system 10 of the present invention. To begin, the eye 20 is maintained in its first configuration wherein it is subjected to a first pressure "$p_1$". Note: this first pressure "$p_1$" may, in fact, result from no externally applied pressure on the eye 20. This condition is indicated by the block 42 of chart 40. Typically, "$p_1$" will be the normal anatomical intraocular pressure of the eye 20. As indicated by block 44, while the eye 20 is in its first configuration, the topography "T" of the anterior surface 24 of the eye 20 is mapped (in this case "$T_{1a}$"). Preferably, this mapping is accomplished by an imaging device 16 of a type well known in the pertinent art. If desired, the topography of the posterior surface 26, "$T_p$", may also be mapped. For purposes of this disclosure, however, the discussion hereinafter is directed primarily to the anterior surface 24. With this in mind, block 46 of chart 40 indicates that the topography "$T_{1a}$" is fitted onto the model 14. Once "$T_{1a}$" is so fitted, mathematical parameters (i.e. numerical representations of biomechanical characteristics at locations in the cornea 22) can be obtained from finite elements of the model 14 (see block 48).

Inquiry blocks 50 and 52 in chart 40 together indicate that once all of the mathematical parameters for the cornea 22 have been obtained for the cornea 22 in its first configuration, consideration can then given to the second configuration. Specifically, inquiry block 54 questions whether a second pressure "$p_2$" has been established. From the above disclosure it will be appreciated that the second pressure "$p_2$" is provided by the pressure device 18, and results from an exertion of the pressure differential 38 (e.g. 10 kPa) against the posterior surface 26 of the cornea 22. Preferably, as the pressure differential 38 is imposed, the second pressure "$p_2$" will be less than about 14 kPa. In any event, this moves the cornea 22 into a second configuration. Block 56 then indicates that the second pressure "$p_2$" is maintained while a second corneal topography "$T_{2a}$" is mapped. Specifically, in this case, a topography "$T_{2a}$" is mapped for the anterior surface 24. Again, if desired, a topography "$T_p$" for the posterior surface 26 can also be mapped. As was previously done with "$T_{1a}$", blocks 44 and 46 indicate the topography "$T_{2a}$" is fitted to the model 14. This time, mathematical parameters (biomechanical characteristics) are obtained for the cornea 22 while it is in its second configuration. Block 52 then indicates that when the tasks of fitting of "$T_{1a}$" and "$T_{2a}$" onto model 14 have been completed, and mathematical parameters are obtained for both the first and second configurations, the operation of system 10 moves to block 58 for an analysis of the collected data 60 (see FIG. 1). Specifically, this is done by comparing various parameters with each other, and with empirical data indicative of a keratoconic condition. It is, of course, possible to obtain a plurality of topographies for the eye 20 under respective pressure conditions. If so, parameters obtained when these topographies are fitted onto the model 14 can be more reliably refined and used with increased precision to obtain a more accurate diagnosis.

Figure 5:
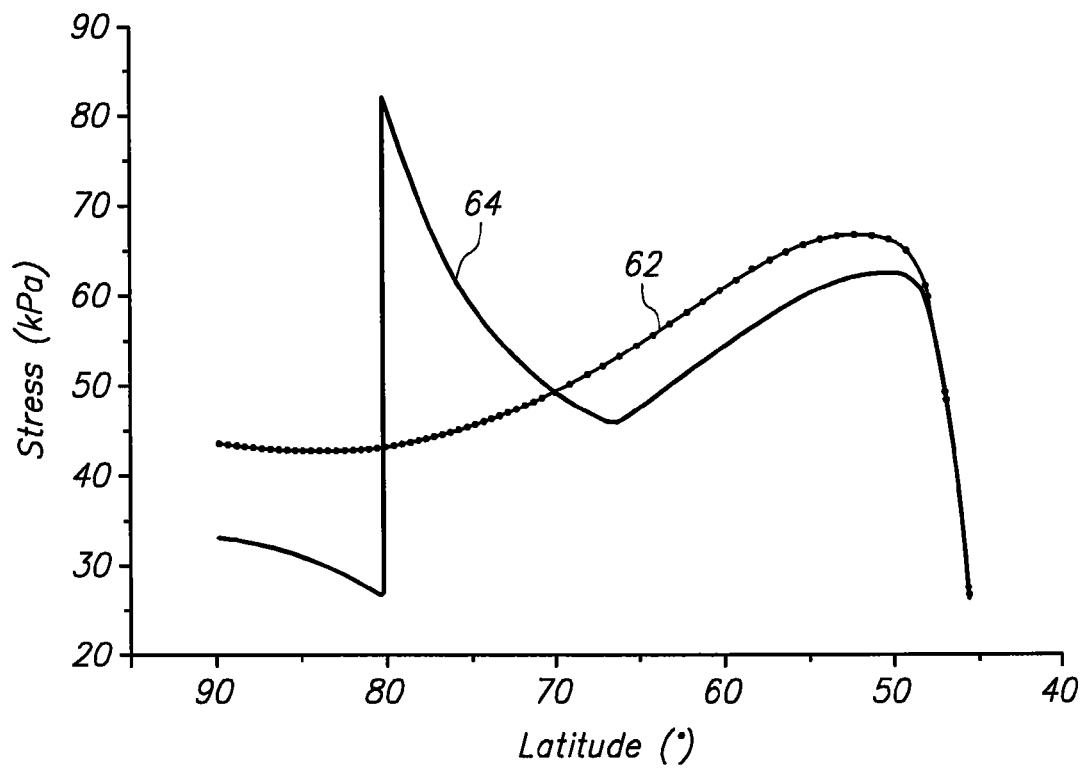
FIG. 5 is a graph showing the relationship of stresses in a healthy eye and in a keratoconic eye.
Figure 6:
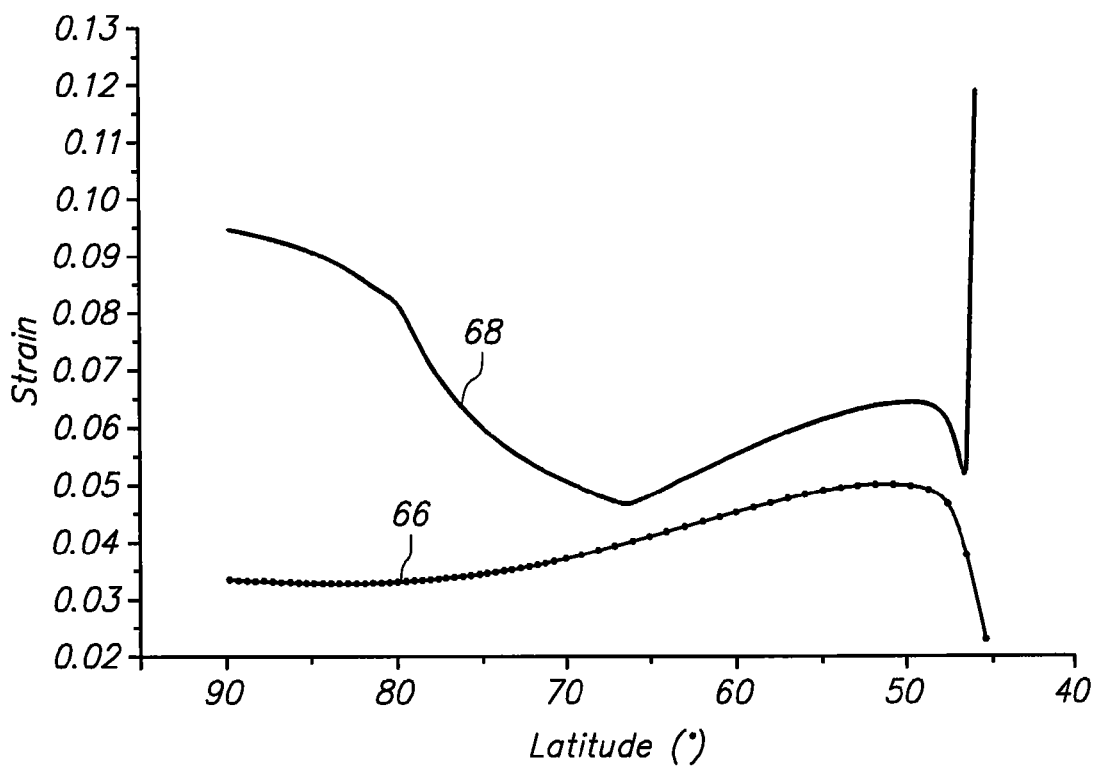
FIG. 6 is a graph showing the relationship of strains in a healthy eye and in a keratoconic eye.

In FIGS. 5 and 6, superposed graphs are shown for the biomechanical stresses (FIG. 5) and strains (FIG. 6) that are respectively expected for a healthy eye 20 and for a keratoconic eye 20. Specifically, the dimpled line 62 in FIG. 5 is indicative of stress changes in the cornea 22, relative to latitude, for a healthy eye 20. On the other hand, the solid line 64 is indicative of stress changes for a keratoconic eye 20. Similarly, the dimpled line 66 in FIG. 6 is indicative of strain changes in the cornea 22, relative to latitude, for a healthy eye 20. And, the solid line 68 in FIG. 6 is indicative of strain changes for a keratoconic eye 20. As intended for the present invention, the data 60 is compared (see block 58 of chart 40 in FIG. 4) by the computer 12. Depending on any correspondence in this comparison with the graphs shown in FIGS. 5 and 6, a determination can be made for the purpose of diagnosing whether the eye 20 is keratoconic.

While the particular Finite Element Model of a Keratoconic Cornea as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for diagnosing a keratoconic cornea in an eye of a patient, prior to onset of keratoconus, which comprises the steps of:
   providing an electronic model of a cornea, wherein the model includes a first plurality of elements representing Bowman's membrane in the cornea, and a second plurality of elements representing the stroma in the cornea, and wherein each element in the model is defined by a plurality of parameters, with each parameter being representative of tissue qualities in the cornea at the corresponding location of the element in the model;
   mapping a topography of the anterior surface of the cornea "$T_a$";
   pressurizing the eye during the mapping step;
   fitting the topography "$T_a$" to the model to obtain a set of parameters for the plurality of elements; and
   evaluating the set of parameters to diagnose whether the cornea is keratoconic.

2. A method as recited in claim 1 further comprising the steps of:
   mapping a topography of the posterior surface of the cornea "$T_p$"; and
   fitting the topography "$T_p$" to the model concurrently with the "$T_a$" fitting step.

3. A method as recited in claim 2 wherein the pressurizing step is accomplished with an increase in intraocular pressure less than approximately 14kPa.

4. A method as recited in claim 3 wherein the pressurizing step is accomplished at a plurality of different pressures.

5. A method as recited in claim 1 wherein the mapping step comprises the step of imaging the anterior surface of the cornea.

6. A method as recited in claim 1 wherein the model is a finite element model.

7. A method for diagnosing a keratoconic cornea in an eye of a patient, prior to onset of keratoconus, which comprises the steps of:
   providing an electronic model of a cornea, wherein the model includes a first plurality of elements representing Bowman's membrane in the cornea, and a second plurality of elements representing the stroma in the cornea, and wherein each element in the model is defined by a plurality of parameters, with each parameter being representative of tissue qualities in the cornea at the corresponding location of the element in the model;
   recording a topography "$T_a$" of the anterior surface of the cornea;
   pressurizing the eye with a predetermined intraocular pressure prior to the recording step;
   fitting "$T_a$" onto the model to obtain a set of parameters from the model, wherein each parameter is indicative of a biomechanical property of tissue at a location in the cornea; and
   evaluating the parameters from the model to diagnose whether the cornea is keratoconic.

8. A method as recited in claim 7 further comprising the steps of:
   repeating the pressurizing step, the recording step and the fitting step to obtain a plurality of sets of parameters, wherein each parameter in each set is indicative of a biomechanical property of tissue at a location in the cornea, and corresponds to a respective parameter at a same location in another set; and
   comparing parameters to improve accuracy of the diagnosis.

9. A method as recited in claim 7 wherein the pressurizing step is accomplished at a pressure less than 14 kPa.

10. A method as recited in claim 9 wherein a change in pressure between different pressurizing steps is greater than approximately 2 kPa.

11. A method as recited in claim 7 further comprising the step of recording a topography "$T_p$" of the posterior surface of the cornea for use in the fitting step.

12. A method as recited in claim 7 wherein the step of recording "$T_a$" comprises the step of imaging the anterior surface of the cornea.

13. A method as recited in claim 7 wherein the model is a finite element model.

14. A system for diagnosing a keratoconic cornea in an eye of a patient which comprises:
   an imaging device for recording a topography "$T_a$" of the anterior surface of the cornea;
   a pressure device for selectively pressurizing the eye during the recording of the topography "$T_a$";
   an electronic model having a plurality of elements, wherein each element in the model is defined by a plurality of parameters, with each parameter being representative of tissue qualities inside the cornea at the corresponding location of the element in the model;
   a computer means for fitting "$T_a$" onto the model to obtain a set of parameters from the model, wherein each parameter is indicative of a biomechanical property of tissue at a location in the cornea; and a comparator for evaluating the set of parameters to diagnose whether the cornea is keratoconic.

15. A system as recited in claim 14 wherein the model is a finite element model comprising:
   a first plurality of elements programmed to be representative of Bowman's membrane in the cornea; and
   a second plurality of elements programmed to be representative of the stroma of the cornea.

16. A system as recited in claim 15 wherein each element of the model corresponds to a location in the cornea of the eye and comprises mathematical parameters representative of biomechanical characteristics of corneal tissue at the respective locations in the cornea.

17. A system as recited in claim 14 wherein the comparator is a component of a computer.

* * * * *